United States Patent [19]

Larock

[11] Patent Number: 4,658,033

[45] Date of Patent: Apr. 14, 1987

[54] SYNTHESIS OF INTERPHENYLENE PROSTAGLANDIN ANALOGS

[75] Inventor: Richard C. Larock, Ames, Iowa

[73] Assignee: Iowa State University Research Foundation, Inc., Ames, Iowa

[21] Appl. No.: 778,803

[22] Filed: Sep. 23, 1985

[51] Int. Cl.$^4$ ................... C07D 307/00; C07C 67/30

[52] U.S. Cl. ........................... 548/123; 544/63; 544/65; 544/235; 548/124; 548/126; 548/217; 548/241; 548/262; 548/369; 548/453; 549/15; 549/32; 549/350; 549/363; 549/426; 549/427; 549/435; 549/463; 560/51; 560/53; 560/57; 560/101; 562/462; 562/466; 562/491; 568/633; 568/659; 568/660; 568/808

[58] Field of Search ............... 549/463, 15, 32, 350, 549/363, 426, 427, 435; 544/63, 65, 235; 548/123, 124, 126, 217, 241, 262, 369, 453; 560/51, 53, 57, 101; 562/462, 466, 491; 568/633, 659, 660, 808; 556/136

[56] References Cited

U.S. PATENT DOCUMENTS

| | | | |
|---|---|---|---|
| 4,020,097 | 4/1977 | Nelson | 560/53 |
| 4,084,058 | 4/1978 | Nelson | 560/55 |
| 4,113,755 | 9/1978 | Larock | 556/136 |
| 4,349,689 | 9/1982 | Aristoff | 560/117 |
| 4,351,949 | 9/1982 | Larock | 560/118 |
| 4,420,632 | 12/1983 | Aristoff | 560/119 |
| 4,436,934 | 3/1984 | Larock | 560/120 |
| 4,463,015 | 7/1984 | Haslanger et al. | 549/463 |
| 4,474,804 | 10/1984 | Das et al. | 549/463 |
| 4,522,949 | 7/1985 | Das et al. | 549/463 |

OTHER PUBLICATIONS

Catellani et al., Tetrahedron Letters, 23 (43), pp. 4517–4520, (1982).

Maitlis, The Org. Chem. of Palladium, vol. 1, Academic Press, p. 72 (1971).

Larock et al, Tetrahedron Letters, 23 (10), pp. 1071–1074 (1982).

*Primary Examiner*—John M. Ford
*Assistant Examiner*—Bernard I. Dentz
*Attorney, Agent, or Firm*—Zarley, McKee, Thomte, Voorhees & Sease

[57] ABSTRACT

New interphenylene prostaglandin (PGH) analogs are prepared by a method which involves reacting a bicyclic olefin, an acetylene compound and a benzylic halide together, in the presence of a palladium(O) catalyst in a single-step synthesis. By this technique a large number of new interphenylene PGH analogs can be prepared, which are useful as inhibitors of arachidonic acid induced platelet aggregation.

14 Claims, No Drawings

SYNTHESIS OF INTERPHENYLENE PROSTAGLANDIN ANALOGS

BACKGROUND OF THE INVENTION

The mammalian hormones known as prostaglandins are an extremely important, biologically active class of $C_{20}$ unsaturated hydroxy acids first discovered in the 1930's. They have been found to have pronounced effects on the cardiovascular, respiratory and renal systems; the gastrointestinal tract; blood platelets and bone; the eye, skin, lungs, and the reproductive organs. They appear to have pharmacological potential in the treatment of nasal congestion, stomach ulcers, hypertension, asthma, inflammation and thrombosis, as well as possible use in the induction of labor, termination of pregnancy, and utility in contraception. To date the major drawbacks to clinical application of the prostaglandins have been the very broad range of physiological activity prevalent in these compounds and their brief duration of action due to rapid metabolic deactivation. The desire for longer lasting drugs exhibiting much more specific activity has recently produced a number of very interesting analogs of prostaglandins and many structure-activity studies have resulted.

Tremendous potential also exists in the development of prostaglandin antagonists and reagents which will inhibit prostaglandin biosynthesis and metabolism. For this reason there has been considerable work of late on the biosynthetic pathways involved in the formation of prostaglandins. This work has resulted in the recent discovery of intermediate prostaglandin endoperoxides and their biosynthetic products prostacyclin and the thromboxanes.

As biologically potent substrates, as well as key intermediates in prostaglandin biosynthesis, the endoperoxides have stimulated considerable recent synthetic effort. Some of these compounds are potent vasoconstrictors, stimulate smooth muscle contraction, induce the aggregation of human blood platelets, and inhibit $PGE_1$, $PGE_2$ and thromboxane biosynthesis.

With the recent discoveries of the highly active but very unstable prostacyclin and thromboxanes, attention has turned towards the synthesis of stable analogs of these compounds. Numerous prostacyclin analogs possessing substantial biological activity are now known. Similarly, the potent blood platelet aggregating and vasoconstrictor properties of thromboxane $A_2$ ($TXA_2$) have inspired other workers to synthesize each of the following stable analogs:

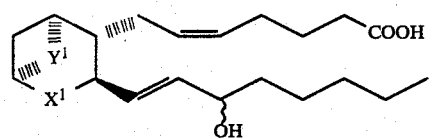

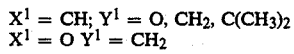

$X^1 = CH; Y^1 = O, CH_2, C(CH_3)_2$
$X^1 = O\ Y^1 = CH_2$

These compounds are inhibitors of $PGH_2$-induced aggregation of human blood platelets; have shown very potent vasoconstricting activity as well as behavior as a potent thromboxane $A_2$ antagonist on platelet aggregation, while selectively inhibiting the biosynthesis of thromboxanes; and selectively inhibit coronary artery constriction, platelet aggregation, and thromboxane formation. The compound with $X^1=CH_2$, $Y^1=C(CH_3)_2$ has been suggested as a suitable antithrombotic agent.

From the above brief review, it should be quite obvious that the natural prostaglandins, the endoperoxides, prostacyclin and the thromboxanes display an extraordinary range of biological activity. The synthesis of stable analogs of these compounds shows tremendous promise of providing new compounds with more specific activity which will prove useful in the treatment of a vast array of human physiological ailments. Most syntheses to date have involved lengthy multistep sequences or have begun with the natural prostaglandins.

The primary objective of the present work is directed towards the development of an entirely new synthetic route to interphenylene PGH (endoperoxide) analogs—a route which provides a large number of new compounds, particularly interphenylene PGH analogs, the general class of which have been demonstrated as useful biologically active compounds, e.g. see my publication, *Tetrahedron Letters*, Vol. 26, No. 23, pp. 2763-2764, 1985, which is incorporated herein by reference, with particular attention being drawn to the articles of footnotes 1-23 for interphenylene analogs.

A further object is to prepare certain compounds of the type previously described which show substantial inhibition of arachidonic acid induced blood platelet aggregation.

The method, compounds and manner of performing the reactions and accomplishing the objectives of this invention are illustrated by the detailed description which follows hereinafter.

DETAILED DESCRIPTION OF THE INVENTION

The present invention relates to novel prostaglandin endoperoxide analogs, and to their production and use.

More particularly, this invention relates to novel interphenylene PGH analogs, to pharmaceutical compositions containing at least one of the compounds, and to a process for the preparation of the compounds. The novel compounds of this invention are represented by the following formula:

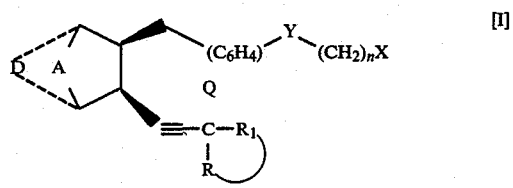

wherein n equals a whole integer of from 1 to 12, X is carboxylic acid, or $C_1$-$C_8$ ester, alcohol, ether, or amide groups; A is methylene, ethylene, oxa, imino, or lower alkyl, phenyl or aryl substituted imino; D is methylene, ethylene, vinylene, methyleneoxy, alkylidenedioxy, iminooxy, dithio, or azo; R and $R_1$ are hydrogen, lower alkyl and lower aryl or $(CH_2)_Z$ with Z being 2 to 5, and Q is hydroxy, methoxy, acetoxy, or hydrogen, or Q and R are both oxo. Y is oxa or methylene. The aryl group ($C_6H_4$) may be ortho, meta or para substituted.

In the significance as used above, it is possible for "n" to be from 1 to 12; however, since in the natural prostaglandins "n"=3, it has been found that the more one moves away from 3, the more unlikely that the compounds would have any specific activity. 1 to 7 are preferred with the most preferred being from 1 to 5, since this most nearly brackets, on both sides, the natural biologically active compounds.

The moiety represented by X is the easiest to change in the structure. It is not critical to the process or the products of this invention, and can be changed by conventional, routine chemistry. Most preferred is a carboxylic acid group since once again the natural prostaglandins have a carboxylic acid group at the X position. With other functional groups such as esters, alcohols, ethers and amides, preferably $C_1$ to $C_8$ groups are employed, and most preferably $C_1$ to $C_5$. "A" is preferably methylene, ethylene or oxygen, but can also be amino, or lower alkyl- phenyl- or aryl- substituted amino groups. The term "lower" refers to having from $C_1$ to $C_8$.

"D" can be methylene, ethylene, vinylene, methyleneoxy, alkylidenedioxy, iminooxy, dithio or azo. D is preferably ethylene or vinylene. "R" and "$R_1$" are hydrogen, lower alkyl and lower aryl, or $(CH_2)_z$, with Z being 2 to 5. The term "lower" is used in the same sense as previously defined.

Finally, "Q" is selected from the group consisting of hydroxy, methoxy, acetoxy, or hydrogen, or Q and R are both oxo. The compounds [I] have been found to possess the property of exhibiting substantial inhibition of arachidonic acid induced platelet aggregation.

The method of synthesis of these interphenylene PGH analogs can be generally summarized as an addition reaction between a bicyclic olefin, an acetylene and a benzylic halide, with the reaction being conducted in the presence of at least a catalytically effective amount of a palladium(O) catalyst. The reaction is advantageous in that it is a single-pot synthesis which occurs in a relatively short time and therefore does not need or use the cumbersome techniques of stepwise synthesis and the attendent inefficiencies thereof. The reaction is straightforward and achieves relatively high yields as measured by the starting amount of olefin, with yields being within the range of from 30% up to nearly 60%. This is considered quite high in prostaglandin synthesis techniques.

Before describing each of the ingredients and the overall reaction, it may be helpful to represent the reaction by a word equation. The reaction in equation form is represented by the following:

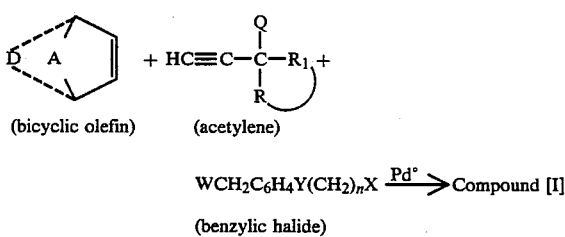

(bicyclic olefin)    (acetylene)

WCH$_2$C$_6$H$_4$Y(CH$_2$)$_n$X $\xrightarrow{Pd^\circ}$ Compound [I]

(benzylic halide)

The bicyclic olefin shown in the above identified equation is the same bicyclic olefin used as a starting material in my previous U.S. Pat. No. 4,351,949, issued Sept. 28, 1982 entitled BICYCLIC PROSTAGLANDIN ANALOGS AND METHOD OF SYNTHESIS. These compounds are either commercially available or readily prepared. A and D are as previously defined. An excess of the readily available bicyclic olefin, usually 4-8 equivalents is usually used, and is therefore preferred.

The second reactant shown above is characterized as an acetylene compound. The formula for the acetylene compound is shown in the above general equation. "Q", "R" and "$R_1$" are as earlier defined.

The final reactant is a benzylic halide, as also represented in the general equation previously presented. In the benzylic halide formula "W" is a halide selected from the group consisting of chloride, bromide, and iodide, "Y" is oxa or methylene, and "n" and "X" are as previously defined. The aryl group ($C_6H_4$) may be ortho, meta or para substituted. The three reactants are simply stirred together in a single-pot synthesis reaction, with the amount of time not being critical, but preferably on the order of 1 or 2 days. Ordinarily, the reaction temperature can be from about 25° C. to about 150° C., preferably from about 70° C. to about 80° C.

Pressure is not critical. The reaction is conducted in the presence of a solvent in order to allow intimate admixture of the reactant ingredients. The precise solvent employed is not critical, but satisfactory results can be obtained with anisole and other standard aprotic solvents such as tetrahydrofuran and the like.

The palladium(O) catalyst employed is also not critical, but the preferred catalyst is tetrakis(triphenylphosphine)palladium(O). The amount of catalyst employed is not critical, as long as it is a catalytically effective amount. As a guideline, amounts from about 3% up to 100% of an equimolar amount of the other reactant ingredients may be employed. Other palladium(O) catalysts may be used such as DBA (dibenzylideneacetone) palladium(O) complexes. The amount of the reactants employed is likewise not critical but generally at least stoichiometric amounts should be employed.

The reaction is generally run under nitrogen but other inert gases which do not destroy the catalyst may be used. An equivalent amount of a base such as anhydrous sodium acetate is also added to destroy the HX (X=Cl, Br or I) generated during the reaction. The base is not critical. Other inorganic bases such as Na$_2$CO$_3$, KOAc, K$_2$CO$_3$ can also be used.

The compounds prepared by the present invention can be administered in intraparenteral or oral dosage forms over a wide dose range, for example from about 0.05 mg/kg weight to about 10 mg/kg weight.

The following examples are offered to further illustrate but not limit the process and product of the present invention.

The three examples set forth below may be summarized as follows: they represent the reaction of norbornene, norbornadiene and 7-oxanorbornene with methyl 3-(chloromethyl) phenoxyacetate, (S)-1-octyn-3-ol and 8% Pd(PPh$_3$)$_4$. They all provide one step satisfactory yields of the corresponding, interphenylene PGH$_2$ analogs.

In particular with the reaction with norbornene equimolar amounts of methyl 3-(chloromethyl)phenoxyacetate, optically active (S)-1-octyn-3-ol(2) and anhydrous sodium acetate, plus 4 equiv. of norbornene and 8% Pd(PPh$_3$)$_4$, when heated to 70° C. for 1 day in anisole provided a 58% isolated yield of an inseparable mixture of the two possible diastereomers of

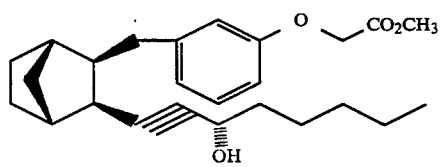

Compounds in accordance with formula [I] were prepared in which Q=OH, R=H, and $R^1=C_5H_{11}$, with A being methylene, and D being ethylene.

The table below lists the amounts of olefin or diene that was used in each synthesis and the temperature conditions. The concentration of the other reagents were kept constant at 1 equiv. 8% of catalytic $Pd(PPh_3)_4$ was used in all cases.

TABLE

| Entry | Olefin or Diene used | Number of Equivalents | Reaction Temperature | Yield |
| --- | --- | --- | --- | --- |
| 1 |  | 4 | 70–75° C. | 58% |
| 2 | 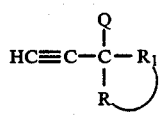 | 8 | 80° C. | 37% |
| 3 |  | 4 | 70–72° C. | 34% |

Hydrolysis of the methyl ester, where appropriate, were carried out with 2M KOH in refluxing methanol for 2 hours. The compound represented in entry number 3 was converted to the acid from the ester by a similar saponification process, with stirring at room temperature for 2 days.

PROCEDURE EXAMPLES 1–3

Experimental: $^1H$ NMR and $^{13}C$ NMR spectra were recorded on a Nicolet NT-300 operating at 300.068 or 75 MHz, respectively. Alternatively, a Varian EM 360A, operating at 60 MHz, was used. IR spectra were recorded on a Beckmann—42050 spectrophotometer. Mass spectral data were obtained from an MS-50 spectrometer. Known compounds used in this research were purchased from Aldrich Chemical Company. Anisole was distilled over sodium and (S)-1-octyn-3-ol was distilled, neat, before use. Sodium acetate was made anhydrous by heating at 110° C. in an oil bath, under vacuum, overnight. Sodium sulfate was used as the drying agent. All glassware was dried in the oven overnight at 140° C. and cooled under a stream of nitrogen before use.

The following procedure was employed in the synthesis of each of the interphenylene PG ester analogs shown in the table above. To a round bottomed flask with a side arm, equipped with a reflux condenser, was introduced under nitrogen $Pd(PPh_3)_4$ (45 mg, 0.039 mmol) and anhydrous sodium acetate (41 mg, 0.5 mmol). A solution of m-chloromethylphenoxyacetic acid methyl ester (107 mg, 0.5 mmol), (S)-1-octyn-3-ol (63 mg, 0.5 mmol) and norbornene (188 mg, 2 mmol) or 7-oxanorbornene (192 mg, 2 mmol) or norbornadiene (368 mg, 4 mmol), in degassed anisole (1 ml) was added to the flask. The mixture was heated at the appropriate temperature (see table) for a day. After cooling, dilute sulfuric acid was added and the solution extracted with diethyl ether. After drying the ether extracts with sodium sulfate, the solvents were removed under vacuum and the residue chromatographed on a silica gel column, using hexanes/ethyl acetate mixtures as the eluent. The products which are colorless oils gave satisfactory spectral data.

The yield of methyl ester (entry 1) was 58%. The yield of methyl ester in entry 2 was 37%, and the yield of ester in entry 3 was 34%.

The compounds prepared in entries 1 and 2 were hydrolyzed to provide PGH interphenylene analogs in the following manner, which is specific for entry 1, with entry 2 being a duplication. The hydroxy ester (55.7 mg, 0.14 mmol) was refluxed for 2 hours in 5 ml of methanol and 1 ml of 2M potassium hydroxide. After cooling, the reaction was diluted with ether, acidified with 25 ml of 2N sulfuric acid, washed with 50 ml of brine and dried over sodium sulfate. Removal of solvent under vacuum and purification by chromatography of the residue with hexanes/ethyl acetate/glacial acetic acid in a 20:20:1 ratio, yielded the pure acid, in a 95% (51.5 mg) yield, as a colorless oil.

For entry 3 the same procedure was followed except that the reaction was run at room temperature for 2 days. The reaction was diluted with ether, acidified with dilute sulfuric acid, washed with brine and dried over sodium sulfate. Removal of solvent under vacuum provided the pure acid in an almost quantitative yield. Further data for each of the hydrolyzed compounds are provided below.

Entry 1 hydrolysis product, 95% yield. $R_f=0.31$ in 20:20:1 hexanes/ethyl acetate/glacial acetic acid.

Entry 2 hydrolysis product, 88% yield. $R_f=0.30$ in 20:20:1 hexanes/ethyl acetate/acetic acid. Entry 3 hydrolysis product, ≃98% yield.

What is claimed is:

1. A method of synthesis of interphenylene PGH analogs, comprising:

reacting a bicyclic olefin of the formula:

wherein A is methylene, ethylene, oxy, imino, or lower alkyl- or aryl- substituted imino; and D is methylene, ethylene, vinylene, methyleneoxy, alkylidenedioxy, iminoxy, dithio or azo, with an acetylene of the formula:

$$HC\equiv C-\underset{\underset{R}{|}}{\overset{\overset{Q}{|}}{C}}-R_1$$

wherein R and $R_1$ are hydrogen, lower alkyl and lower aryl or $(CH_2)_Z$ with the Z being 2–5, Q being hydroxy, methoxy, acetoxy, or hydrogen or Q and R are oxo, and with a benzylic halide of the formula:

W $CH_2$ $C_6H_4$ $Y(CH_2)_nX$ wherein W is a halide selected from the group of chloride, bromide, and iodide, Y is oxa or methylene, n is 1–12, X is a carboxylic acid or $C_1$-$C_8$ ester, alcohol, ether or amide group and the aryl group ($C_6H_4$) is ortho, meta or para substituted, said reaction being conducted in the presence of a catalytically effective amount of a palladium(O) catalyst to provide an interphenylene PGH analog of the formula

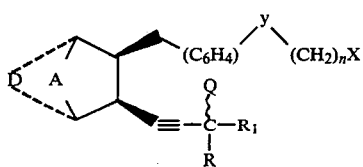

wherein, A, D, R, $R_1$, Q, Y and n are as previously defined.

2. The process of claim 1 wherein n is from 1 to 7.

3. The process of claim 1 wherein X is a carboxylic acid group or ester.

4. The process of claim 1 wherein D is selected from the group of ethylene or vinylene.

5. The process of claim 1 wherein at least stoichiometric amounts of each reactant are employed except for the palladium catalyst.

6. The process of claim 1 wherein the reaction is conducted in the presence of a solvent for said reactants.

7. The process of claim 1 wherein the reaction temperature is from about 70° C. to about 80° C.

8. The process of claim 1 wherein the palladium (O) catalyst is tetrakis(triphenylphosphine) palladium (O).

9. The process of claim 1 wherein the palladium (O) catalyst is a dibenzylideneacetone palladium(O) complex.

10. The process of claim 1 wherein A is methylene.

11. The process of claim 1 wherein A is an aryl substituted imino group.

12. The process of claim 11 wherein the aryl group is meta substituted.

13. The process of claim 1 wherein W is chloride.

14. The process of claim 1 wherein Q is hydroxy.

* * * * *